United States Patent
Chen et al.

(10) Patent No.: US 12,201,076 B2
(45) Date of Patent: Jan. 21, 2025

(54) **METHOD FOR OBTAINING REGENERATED SEEDLINGS OF *BRASSICA CAMPESTRIS L.SSP.CHINENSIS* FROM EMBRYONIC TIP TISSUE**

(71) Applicants: Anhui Agricultural University, Hefei (CN); Yingshang Shili Ecological Agriculture Technology Co., Ltd., Fuyang (CN)

(72) Inventors: Guohu Chen, Hefei (CN); Qian Yin, Hefei (CN); Ting Li, Hefei (CN); Chenggang Wang, Hefei (CN); Xiaoyan Tang, Hefei (CN); Ying Wang, Hefei (CN); Xueqing Liu, Hefei (CN); Hongwei Wen, Hefei (CN); Siwen Wu, Hefei (CN)

(73) Assignees: Anhui Agricultural University, Hefei (CN); Yingshang Shili Ecological Agriculture Technology Co., Ltd., Fuyang (CN)

( * ) Notice: Subject to any disclaimer, the term of this patent is extended or adjusted under 35 U.S.C. 154(b) by 0 days.

(21) Appl. No.: 18/651,494

(22) Filed: Apr. 30, 2024

(65) Prior Publication Data
US 2024/0284846 A1  Aug. 29, 2024

(30) Foreign Application Priority Data
Jun. 8, 2023 (CN) .......................... 202310675627.6

(51) Int. Cl.
*A01H 4/00* (2006.01)
(52) U.S. Cl.
CPC ............. *A01H 4/008* (2013.01); *A01H 4/002* (2021.01)
(58) Field of Classification Search
CPC .................................................. A01H 4/008
See application file for complete search history.

(56) References Cited

FOREIGN PATENT DOCUMENTS

| | | | |
|---|---|---|---|
| CN | 101530062 A | * | 9/2009 |
| CN | 102144561 A | | 8/2011 |
| CN | 104115751 A | | 10/2014 |
| CN | 109258466 A | * | 1/2019 |
| CN | 111727885 A | | 10/2020 |
| CN | 116569842 B | * | 1/2024 ............. A01H 4/002 |

OTHER PUBLICATIONS

Green Business Light_2024. (Year: 2024).*
Fuller et al (Plant tis sue culture using Brassica seedlings. Journal of Biological Education. p. 53-59, 1995). (Year: 1995).*
Sivanandhan et al (High Frequency in vitro Regeneration of Chinese cabbage (cv. Kenshin) from Hypocotyl and Cotyledon Explants. Horticultural Science and Technology 37: p. 640-650, 2019). (Year: 2019).*
Lihua Zhu et al., "Studies on High Efficient System for in vitro Shoot Regeneration from Hypocotyls of Chinese Cabbage", Journal of Wuhan Botanical Research, 2005, vol. 23, No. 5, pp. 427-431.
Guohu Chen et al., "Establishment of Effective Regeneration System of Wucai in vitro", Molecular Plant Breeding, 2017, vol. 15, No. 4, pp. 1466-1472.

* cited by examiner

*Primary Examiner* — Charles Logsdon
*Assistant Examiner* — Wayne Zhong

(57) ABSTRACT

A method for obtaining regenerated seedlings of *Brassica campestris* L. ssp. *chinensis* from embryonic tip tissues, including the following steps. A seed is inoculated to a germination medium for dark culture for 60 h. The testa, root tip, two cotyledons and middle growing point of the resultant germinated seed are removed, and an embryonic tip with a length of 3-5 mm is retained as an explant. The explant is sequentially subjected to low-temperature pre-culture in a pre-culture medium for 36 h, room-temperature shaking culture in a liquid bud induction culture medium for 10 min, and bud induction culture in a bud induction culture medium for 20 d. A regenerated plant with 5-6 leaves is transferred to a rooting medium for rooting culture for about 2 weeks, and a well-rooted plant is collected, and subjected to hardening and transplantation into a filed.

1 Claim, 1 Drawing Sheet

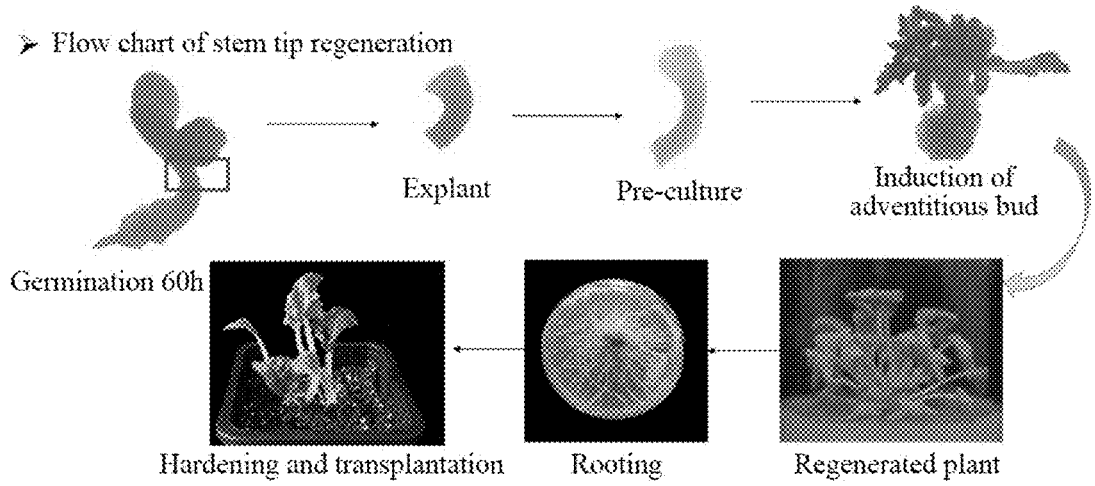

METHOD FOR OBTAINING REGENERATED SEEDLINGS OF *BRASSICA CAMPESTRIS L.SSP.CHINENSIS* FROM EMBRYONIC TIP TISSUE

CROSS-REFERENCE TO RELATED APPLICATIONS

This application claims the benefit of priority from Chinese Patent Application No. 202310675627.6, filed on Jun. 8, 2023. The content of the aforementioned application, including any intervening amendments thereto, is incorporated herein by reference in its entirety.

TECHNICAL FIELD

This application relates to plant tissue culture technology, and more particularly to a method for obtaining regenerated seedlings of *Brassica campestris* L. ssp. *chinensis* from embryonic tip tissue.

BACKGROUND

*Brassica campestris* L. ssp. *chinensis* is a non-heading Chinese cabbage, and is a vegetable of *Brassica campestris* L. ssp. *chinensis* Makino, also known as Wuta-cai, Tatacai and Heicai. *Brassica campestris* L. ssp. *chinensis* is widely planted in Jianghuai area of China and is a main vegetable in winter. With a cultivation history of nearly a thousand years, *Brassica campestris* L. ssp. *chinensis* is an ideal vegetable to adjust the shortage in winter and spring before and after the Spring Festival, and plays an indispensable role in promoting the development of local agricultural economy. And *Brassica campestris* L. ssp. *chinensis* is also called "vitamin vegetable" owing to it is rich in vitamins.

With the development of biotechnology, people pay more and more attention to improving crop traits through the biotechnology. Breeding by the plant genetic engineering, as an advanced technology for efficient improvement of crop trait, has been widely used. However, the plant genetic engineering depends on an efficient tissue culture regeneration system, and tissue culture regeneration efficiency directly determines success of genetic transformation. Therefore, it is of great significance to build the efficient tissue culture regeneration system and obtain regenerated seedlings quickly for improving the traits of *Brassica campestris* L. ssp. *chinensis* by utilizing the plant genetic engineering.

A tissue culture regeneration system of *Brassica campestris* L. ssp. *chinensis* is basically divided into four stages: obtaining an aseptic seedling, cutting and pre-culturing an explant, inducing an adventitious bud, and rooting and acclimating into seedling, etc., involving different selections of explant, different pre-culture mediums, different pre-culture time, different bud induction culture mediums and different rooting culture mediums, etc. Among them, the selection of explant, pre-culture and the bud induction culture mediums have great influence on the success and efficiency of tissue regeneration. Former studies mainly used cotyledon with petiole or hypocotyl as the explant to build the regeneration system, however such generation system has problems of low regeneration efficiency and long cycle time.

Current tissue regeneration methods for the Chinese cabbage vegetables includes: Jiazheng Yuan, Chunming Wang, Li Shi, Weichang Yu, Method for Building Regeneration System of Pakchoi in vitro (Chinese Patent Application No. 201811189960); Lihua Zhu, Research on Efficient Adventitious Bud Regeneration in vitro of Chinese Cabbage Hypocotyl (Master's Thesis, Nanjing Agricultural University, 2005); Guohu Chen, Shengyun Zhang, Lingyun Yuan, Shidong Zhu, Shan Liu, Hui Zhang, Chenggang Wang. Establishment of Effective Regeneration System of Wucai in vitro, *Mol Plant Breed*, 2017; Lugang Zhang, Xuecheng Liu, Lei Ru, Haiping Li, Maixia Hui, Mingke Zhang, Culture Method for Regeneration in vitro of Chinese Cabbage True Leaf (Chinese Patent Application No. 201110045595.9); Lugang Zhang, Aili Fan, Yunxia Wu, Huiling Qu, Maixia Hui, Mingke Zhang, Tissue Culture Method for Orange Chinese Cabbage with Cotyledon Segment as Explant in vitro (Chinese Patent Application No. 200810232067.2); and Qianqian Liu, Weixin Liu, Culture Method for Obtaining Regenerated Plant from Chinese Cabbage Heading Leaf (Chinese Patent Application No. 201410364506.0).

The prior art above has the following defects.

(1) According to Method for Building Regeneration System of Pakchoi in vitro, the cotyledon is used as the explant, but the method has complicated operation, multiple types of hormones, relatively low induction rate (57.6%) and relatively high proportion of deformed bud in regenerated buds, and does not build a efficient regeneration system.

(2) According to Research on Efficient Adventitious Bud Regeneration in vitro of Chinese Cabbage Hypocotyl, a regeneration system of Chinese cabbage hypocotyl is built. But only relevant factors, such as hormones and explant are optimized, and the regeneration time of the adventitious bud is about 3 weeks.

(3) According to Establishment of Effective Regeneration System of Wucai in vitro, the cotyledon, as the explant, is used to obtain relatively high regeneration efficiency. The induction rate of the adventitious bud can reach 85.56%, but the regeneration time of the adventitious bud is over 4 weeks, which is relatively long. And the average number of the adventitious buds per explant is relatively low 5.36.

(4) According to Culture Method for Regeneration in vitro of Chinese Cabbage True Leaf, the true leaf of Chinese cabbage is used to regenerate. According to Tissue Culture Method for Orange Chinese Cabbage with Cotyledon Segment as Explant in vitro, the cotyledon segment of Chinese cabbage is used as the explant to regenerate. And according to Culture Method for Obtaining Regenerated Plant from Chinese Cabbage Heading Leaf, the heading leaf of Chinese cabbage is used as the explant to regenerate in vitro. Although these methods successfully build tissue culture regeneration systems, these methods have complicated operation, long culture cycle and large workload.

The methods above have the following commonality. The cotyledon, the hypocotyl and the true leaf are used as the explants. The regeneration time of the adventitious bud is long, and part of the methods has low regeneration efficiency. A large number of regenerated seedlings cannot be obtained in a short time. And the optimization factors are not comprehensive.

SUMMARY

In order to overcome the defects of the prior art, this application provides a method for obtaining regenerated seedlings of *Brassica campestris* L. ssp. *chinensis* from an embryonic tip tissue to solve problems of low tissue culture efficiency of *Brassica campestris* L. ssp. *chinensis* and long cycle.

Technical solutions of the present disclosure are described as follows.

This application provides a method for obtaining regenerated seedlings of *Brassica campestris* L. ssp. *chinensis* from an embryonic tip tissue, comprising:

(S1) obtaining an aseptic seed;

(S2) inoculating the aseptic seed obtained in step (S1) into a germination culture medium for dark culture;

(S3) collecting a germinated seed; removing testa, root tip, two cotyledons and a middle growing point from the germinated seed; retaining an embryonic tip with a length of 3-5 mm as an explant;

(S4) subjecting the explant to pre-culture in a pre-culture medium to obtain a primarily-cultured explant;

(S5) subjecting the primarily-cultured explant to shaking culture in a first bud induction culture medium to obtain a secondarily-cultured explant; wherein the shaking culture is performed at room temperature under a rotating speed of 180 rpm for 10 min; the first bud induction culture medium is a Murashigeand Skoog (MS) culture medium containing 3 wt. % of sucrose, 0.8 mg/L of 6-benzylaminopurine (6-BA), 0.2 mg/L of naphthaleneacetic acid (NAA) and 2 mg/L of isopentenyl adenine, and has a pH of 5.8;

(S6) transferring the secondarily-cultured explant to a second bud induction culture medium for bud induction;

(S7) collecting a regenerated plant with 5-6 leaves obtained in step (S6), and transferring the regenerated plant to a rooting culture medium for rooting culture; and (S8) collecting a well-rooted plant obtained in step (S7), and subjecting the well-rooted plant to hardening followed by transplantation into a filed.

In an embodiment, the step (S2) is performed as follows: inoculating the aseptic seed obtained in step (S1) into the germination culture medium for the dark culture for 60 h; wherein the germination culture medium is an MS culture medium containing 3 wt. % of sucrose, 1.0 mg/L of 6-BA and 0.8% agar, and has a pH of 5.8, and the dark culture is performed at a day temperature of 24° C., a night temperature of 18° C. and a humidity of 80%.

In an embodiment, the step (S4) is performed as follows: subjecting the explant to the pre-culture in the pre-culture medium for 36 h; wherein pre-culture is performed at a day temperature of 18° C. and a night temperature of 12° C., a day light-exposure length of 16 h, a night light-exposure of 8 h, a light intensity of 3000 Lx and a humidity of 80%, and the pre-culture medium is an MS culture medium containing 3 wt. % of sucrose, 2.0 mg/L of 6-BA, 0.4 mg/L of 2,4-dichlorophenoxyacetic acid (2,4-D) and 0.8 wt. % of agar, and has a pH of 5.8.

In an embodiment, in step (S6), the second bud induction culture medium is an MS culture medium containing 0.8 mg/L of 6-BA, 0.2 mg/L of NAA, 0.8 wt. % of agar and 3% of sucrose, and has a pH of 5.8; and culture conditions of the bud induction are listed as follows: culture time: 20 days; day temperature: 24° C.; night temperature: 18° C.; day light-exposure length: 16 hours; night light-exposure length: 8 hours; light intensity: 3000 Lx; and humidity: 80%.

In an embodiment, in step (S7), culture conditions of the rooting culture are listed as follows: culture time: 2 weeks; day temperature: 24° C.; night temperature: 18° C.; day light-exposure length: 16 hours; night light-exposure length: 8 hours; light intensity: 3000 Lx; and humidity: 80%; and the rooting culture medium is an MS culture medium containing 3 wt. % of sucrose, 1.0 mg/L of indole butyric acid (IBA) and 0.8 wt. % of agar, and has a pH of 5.8.

Compared to the prior art, the present disclosure has the following beneficial effects.

(1) The method of the present disclosure uses the embryonic tip as the explant to quickly and efficiently obtain the regenerated seedlings of *Brassica campestris* L. ssp. *chinensis*, which significantly shortens regeneration time of tissue culture of Chinese cabbage vegetables.

(2) Utilizing the embryonic tip as the explant for shaking culture before the bud induction, the induction efficiency of adventitious buds and the number of the adventitious buds per explants are significantly improved.

(3) Compared with tissue regeneration of other explants, such as a cotyledon petiole and a hypocotyl, the generation of the explant of the embryonic tip of *Brassica campestris* L. ssp. *chinensis* has short regeneration time, relatively high regeneration efficiency and simple operation, and can saves a lot of manpower and material resources.

(4) A new tissue regeneration scheme for Chinese cabbage vegetables is provided, which can obtain a large number of adventitious buds in a short time, and has more efficient regeneration efficiency, providing a solid foundation for the research of genetic transformation system of *Brassica campestris* L. ssp. *chinensis*.

BRIEF DESCRIPTION OF THE DRAWINGS

FIG. 1 is a flow chart diagram of a method for obtaining regenerated seedlings of *Brassica campestris* L. ssp. *chinensis* from an embryonic tip tissue according to an embodiment of the present disclosure.

DETAILED DESCRIPTION OF EMBODIMENTS

The present disclosure will be clearly and completely described below with reference to the embodiments. It is obvious that the embodiments described herein are only part of embodiments of the present disclosure rather than all embodiments. And any other embodiments made by those skilled in the art based on the embodiments of the present disclosure without creative effort shall fall within the scope of the present disclosure.

In this embodiment, a method for obtaining regenerated seedlings of *Brassica campestris* L. ssp. *chinensis* from an embryonic tip tissue of the present disclosure is verified by *Brassica campestris* L. ssp. *chinensis* var. *communis*.

Referring to FIG. 1, the method for obtaining regenerated seedlings of *Brassica campestris* L. ssp. *chinensis* from an embryonic tip tissue is provided, including the following steps.

Plump and consistent seeds of *Brassica campestris* L. ssp. *chinensis* var. *communis* are selected, washed with sterile water twice and disinfected by blowing with a pipette with 70% of alcohol for 30 s. Then the seeds are shaken and soaked with a 2 wt. % sodium hypochlorite solution for 15 min followed by washing with sterile water 5-6 times and blow-drying on sterile filter paper.

(1) The seeds are inoculated, by sterile tweezers, into a germination culture medium for dark culture, the germination culture medium is a Murashige and Skoog (MS) culture medium containing 3 wt. % of sucrose, 1.0 mg/L of 6-benzylaminopurine (6-BA) and 0.8 wt. % of agar, has a pH of 5.8. And the dark culture is performed at a day temperature of 24° C., a night temperature of 18° C. and a humidity of 80%.

(2) After 60 h of the dark culture, germinated seeds from the step (S1) are collected. Testa, root tip, two cotyledons and middle growing point from each of the germinated seeds are removed by a scalpel. And embryonic tips of the germinated seeds with a length of about 3-5 mm are retained as explants.

(3) The explants are subjected to pre-culture in a pre-culture medium for 36 h to obtain primarily-cultured explants. The pre-culture medium is an MS culture medium containing 3 wt. % of sucrose, 2.0 mg/L of 6-BA, 0.4 mg/L of 2,4-dichlorophenoxyacetic acid (2,4-D) and 0.8 wt. % of agar, and has a pH of 5.8. And the pre-culture is performed at a day temperature of 18° C., a night temperature of 12° C., a day light-exposure length of 16 h, a night light-exposure length of 8 h, a light intensity of 3000 Lx, and a humidity 80%.

(4) The primarily-cultured explants are subjected to shaking culture in a first bud induction culture medium for 10 min to obtain secondarily-cultured explants. And the first bud induction culture medium is an MS culture medium containing 3 wt. % of sucrose, 0.8 mg/L of 6-BA, 0.2 mg/L of naphthaleneacetic acid (NAA) and 2 mg/L of isopentenyl adenine, and has a pH of 5.8.

(5) The secondarily-cultured explants are transferred into a second bud induction culture medium for bud induction. The second bud induction culture medium is an MS culture medium containing 0.8 mg/L of 6-BA, 0.2 mg/L of NAA, 0.8 wt. % of agar and 3 wt. % of sucrose, and has a pH of 5.8. And culture conditions of the bud induction are listed as follows: culture time: about 20 days; day temperature: 24° C.; night temperature: 18° C.; day light-exposure length: 16 hours; night light-exposure length: 8 hours; light intensity: 3000 Lx; and humidity: 80%.

(6) Regenerated plants with 5-6 leaves from step (S5) are collected and transferred to a rooting culture medium for rooting culture. The rooting culture medium is an MS culture medium containing 3 wt. % of sucrose, 1.0 mg/L of indole butyric acid (IBA) and 0.8 wt. % of agar, and has a pH of 5.8. And culture conditions of the rooting culture are listed as follows: culture time: about 2 weeks; day temperature: 24° C.; night temperature: 18° C.; day light-exposure length: 16 hours; night light-exposure length: 8 hours; light intensity: 3000 Lx; and humidity: 80%.

Finally, well-rooted plants from step (S6) are collected and subjected to hardening and transplantation into a filed.

In order to show that the regenerated seedlings cultivated by the method above have short tissue culture period and high efficiency, specific embodiments of the present disclosure are provided below, and individual specific embodiments were performed in triplicate each involving at least 30 explants.

Embodiment 1 Analysis of Influence of Germination Culture Medium Component and Culture Duration on Adventitious Bud Induction of Explants (1) Influence of Germination Culture Medium Component on Bud Induction of Embryonic Tip Explants Plump and consistent seeds of Brassica campestris L. ssp. chinensis var. communis were selected, washed with sterile water twice and disinfected by blowing with a pipette with 70% of alcohol for 30 s. Then the seeds were shaken and soaked with a 2 wt. % of sodium hypochlorite solution for 15 min followed by washing with sterile water 5-6 times and blow-drying on sterile filter paper. Then the seeds were inoculated, by sterile tweezers, into germination culture mediums for dark culture with different 6-BA concentrations. The germination culture mediums were MS culture mediums containing 3 wt. % of sucrose, 0-2.0 mg/L of 6-BA and 0.8 wt. % of agar, and have a pH of 5.8. And the dark culture was performed at day temperature of 24° C. and a night temperature of 18° C.

After 72 h of the dark culture, aseptic seedlings were collected. Testa, root tip, two cotyledons and middle growing point from each of the aseptic seeds were removed by a scalpel. And embryonic tips of the aseptic seedlings with a length of about 3-5 mm were subjected to bud induction in a bud induction culture medium. The bud induction culture medium is an MS culture medium containing 3 wt. % of sucrose, 0.8 mg/L of 6-BA, 0.2 mg/L of NAA and 0.8 wt. % of agar, and has a pH of 5.8. The bud induction was performed at a day temperature of 24° C., a night temperature of 18° C., a day light-exposure length of 16 h, a night light-exposure length of 8 h, a light intensity of 3000 Lx, and a humidity of 80. For individual groups, at least 30 explants were selected, and each treatment was performed in triplicate. Bud induction efficiency and average number of adventitious buds per explants were observed, and influence of germination culture medium on adventitious bud induction was analyzed.

TABLE 1

Influence of Germination Culture Medium Component on Bud Induction of Embryonic Tips Explants

| 6-BA concentrations of MS culture medium (mg/L) | Induction efficiency of adventitious buds/% | Average number of adventitious buds per explants |
|---|---|---|
| 0 | 26.03 ± 1.13 b | 1.23 ± 0.12 b |
| 1 | 36.00 ± 1.80 a | 1.73 ± 0.03 a |
| 2 | 22.67 ± 0.77 b | 1.30 ± 0.15 b |

The letters "a" and "b" indicate significant difference at $P<0.05$.

Referring to Table 1, when 1 mg/L of 6-BA was added into the germination culture medium, the induction efficiency of adventitious buds reached 36.00%, and the average number of adventitious buds per explants reached 1.73. Subsequent experiments were conducted on the seed germination culture medium with the same 6-BA concentration, that is, an MS culture medium containing 3 wt. % of sucrose, 1.0 mg/L of 6-BA and 0.8 wt. % of agar with a pH of 5.8.

(2) Influence of Culture Duration on Adventitious Bud Induction of Embryonic Tips as Explants The aseptic seedlings from the dark culture with different culture duration (the germination culture mediums for the dark culture were determined in (1)) were collected and cut to obtain the embryonic tip explants. The embryonic tip explants were inoculated into the bud induction culture medium for bud induction, and the bud induction culture medium was an MS culture medium containing 3 wt. % of sucrose, 0.8 mg/L of 6-BA, 0.2 mg/L of NAA and 0.8% agar, and has a pH of 5.8. And conditions of the bud induction were listed as follows: day temperature: 24° C.; night temperature: 18° C.; day light-exposure length: 16 hours; night light-exposure length: 8 hours; light intensity: 3000 Lx; and humidity: 80%. For individual groups, at least 30 explants were selected, and each treatment was performed in triplicate. The bud induction efficiency and the average number of adventitious buds per explants were observed, and influence of ages of aseptic seedlings on embryonic tip explants was analyzed.

TABLE 2

Influence of Ages of Explants on Embryonic Tips of Adventitious Buds

| Seedling age of explants (h) | Induction efficiency of adventitious buds/% | Average number of adventitious buds per explants |
| --- | --- | --- |
| 24 | 26.43 ± 2.14 c | 1.97 ± 0.26 d |
| 36 | 29.77 ± 0.77 c | 2.53 ± 0.15 c |
| 48 | 35.07 ± 1.26 b | 3.53 ± 0.09 b |
| 60 | 47.33 ± 0.54 a | 4.40 ± 0.15 a |
| 72 | 37.63 ± 0.58 b | 3.60 ± 0.25 b |

The letters "a", "b", "c" and "d" indicate significant difference at $P<0.05$.

Referring to Table 2, different seedling ages have significant influence on the induction efficiency of adventitious buds and the average number of adventitious buds per explants. Adventitious buds with 60 h of seedling age have the highest induction efficiency of 47.33% and most average number of adventitious buds per explants of 4.40. And aseptic seedlings with 60 h of seedling age were selected for subsequent experiments.

Embodiment 2 Influence of Pre-Culture on Adventitious Bud Induction of Embryonic Tip Explants In this embodiment, Plump and consistent seeds of *Brassica campestris* L. ssp. *chinensis* var. *communis* were selected, washed with sterile water twice and disinfected by blowing with a pipette with 70% of alcohol for 30 s. Then the seeds were shaken and soaked with a 2 wt. % of sodium hypochlorite solution for 15 min followed by washing with sterile water 5-6 times, and blow-drying on sterile filter paper to obtain aseptic seeds. Then the aseptic seeds were inoculated, by sterile tweezers, into a germination culture medium for dark culture, and the germination culture medium was an MS culture medium containing 3 wt. % of sucrose, 1.0 mg/L of 6-BA, 0.8 wt. % of agar, and has a pH of 5.8. And the dark culture is performed at a day temperature of 24° C., a night temperature of 18° C. and a humidity of 80%. After 60 h of the dark culture, germinated seeds from the dark culture were collected. Testa, root tip, two cotyledons and middle growing point from each of the germinated seeds were removed by a scalpel. And embryonic tips of the germinated seeds with a length of about 3-5 mm were retained as explants.

The explants were analyzed as follows.

(1) Influence of Pre-Culture Component and Culture Duration on Adventitious Bud Induction of Embryonic Tip Explants The explants were divided into multiple groups and were inoculated into pre-culture mediums with different concentrations of 6-BA and 2,4-D for pre-culture to obtain primarily-cultured explants, and the pre-culture mediums were MS culture mediums containing 3 wt. % of sucrose, 1.5-2.5 mg/L of 6-BA, 0.2-0.6 mg/L of 2,4-D, 0.8 wt. % of agar, and had a pH of 5.8. Conditions of the pre-culture were listed as follows: culture time: 24-48 h; day temperature: 18° C.; night temperature: 12° C.; day light-exposure length: 16 hours; night light-exposure length: 8 hours; light intensity: 3000 Lx; and humidity: 80%.

The primarily-cultured explants were transferred into a bud induction culture medium for bud induction, and the bud induction culture medium was an MS culture medium containing 3 wt. % of sucrose, 0.8 mg/L of 6-BA, 0.2 mg/L of NAA and 2 mg/L of isopentenyl adenine, and had a pH of 5.8. Conditions of the bud induction were listed as follows: day temperature: 24° C.; night temperature: 18° C.; day light-exposure length: 16 hours; night light-exposure length: 8 hours; light intensity: 3000 Lx; and humidity: 80%. For individual groups, at least 30 explants were selected, and each treatment was performed in triplicate. Bud induction efficiency and average number of adventitious buds per explants were observed, and influence of pre-culture component and culture duration on adventitious bud induction of embryonic tip explants was analyzed.

TABLE 3

Influence of Pre-culture Component and Culture Duration on Adventitious Bud Induction of Embryonic Tip Explants

| 6-BA concentration (mg/L) | 2,4-D concentration (mg/L) | Time (h) | Induction efficiency of adventitious buds/% | Average number of adventitious buds per explants |
| --- | --- | --- | --- | --- |
| 1.5 | 0.2 | 24 | 36.17 ± 1.96 d | 2.73 ± 0.32 de |
| 1.5 | 0.4 | 48 | 41.03 ± 1.49 d | 4.00 ± 0.20 c |
| 1.5 | 0.6 | 36 | 50.00 ± 0.92 c | 4.00 ± 0.10 c |
| 2 | 0.2 | 48 | 54.97 ± 0.47 bc | 5.03 ± 0.29 b |
| 2 | 0.4 | 36 | 66.17 ± 4.02 a | 5.93 ± 0.26 a |
| 2 | 0.6 | 24 | 58.23 ± 1.22 b | 5.00 ± 0.21 b |
| 2.5 | 0.2 | 36 | 56.30 ± 3.33 bc | 4.37 ± 0.12 bc |
| 2.5 | 0.4 | 24 | 51.07 ± 1.35 c | 3.17 ± 0.22 d |
| 2.5 | 0.6 | 48 | 40.00 ± 2.56 d | 2.30 ± 0.17 e |

The letters "a", "b", "c", "d" and "e" indicate significant difference at $P<0.05$.

Referring to Table 3, different concentrations of 6-BA and 2,4-D and different pre-culture durations have significant influence on the induction efficiency of adventitious buds and the average number of adventitious buds per explants. When the pre-culture was performed for 36 h with 2.0 mg/L of 6-BA and 0.4 mg/L of 2,4-D, the pre-culture medium had a highest induction efficiency of adventitious buds of 66.17% and the average number of adventitious buds per explants of 5.93. And subsequent experiments were conducted with the pre-culture medium, that is, an MS culture medium containing 3 wt. % of sucrose, 2.0 mg/L of 6-BA, 0.4 mg/L of 2,4-D and 0.8 wt. % of agar with a pH of 5.8.

(2) Influence of Pre-Culture Temperature on Adventitious Bud Induction of Embryonic Tip Explants The explants were inoculated into the pre-culture medium to obtain primarily-cultured explants, and the pre-culture medium was the MS culture medium containing 3 wt. % of sucrose, 2.0 mg/L of 6-BA, 0.4 mg/L of 2,4-D and 0.8% agar with the pH of 5.8. And the explants were divided into a first group and a second group. The first group was subjected to pre-culture for 36 h at a day temperature of 18° C. and a night temperature of 12° C. The second group was subjected to pre-culture for 36 h at a day temperature of 24° C. and a night temperature of 18° C. The first group and the second group were both subjected to pre-culture at a day light-exposure length of 16 h, a night light-exposure length of 8 h, a light intensity of 3000 Lx, and a humidity 80%.

The primarily-cultured explants were transferred into the bud induction culture medium for bud induction, and the bud induction culture medium was an MS culture medium containing 3 wt. % of sucrose, 0.8 mg/L of 6-BA, 0.2 mg/L of NAA, 0.8 wt. % of agar with a pH of 5.8. Culture conditions of the bud induction were listed as follows: day temperature: 24° C.; night temperature: 18° C.; day light-exposure length: 16 hours; night light-exposure length: 8 hours; light intensity: 3000 Lx; and humidity: 80%. For individual groups, at least 30 explants were selected, and each treatment was performed in triplicate. Bud induction efficiency and average number of adventitious buds per explants were observed, and influence of pre-culture temperature on adventitious bud induction of embryonic tip explants was analyzed.

TABLE 4

Influence of Pre-Culture Temperature on Adventitious Bud Induction of Embryonic Tip Explants

| Temperature (° C.) | Induction efficiency of adventitious buds (%) | Average number of adventitious buds per explants |
| --- | --- | --- |
| Low temperature 18/12 | 66.17 ± 4.02 a | 5.93 ± 0.26 a |
| Room temperature 24/18 | 38.89 ± 6.93 b | 4.13 ± 0.17 b |

The letters "a" and "b" indicate significant difference at $P<0.05$.

Referring to Table 4, the induction efficiency of adventitious buds at the low temperature is significantly higher than that at the room temperature, and the average number of adventitious buds per explants at the low temperature is significantly higher than that at the room temperature. And subsequent experiments were conducted at the low temperature for the pre-culture.

Embodiment 3 Influence of Adventitious Bud Induction Culture on Adventitious Bud Induction of Embryonic Tip Explants In this embodiment, plump and consistent seeds of *Brassica campestris* L. ssp. *chinensis* var. *communis* were selected, washed with sterile water twice and disinfected by blowing with a pipette with 70% of alcohol for 30 s. Then the seeds were shaken and soaked with a 2 wt. % of sodium hypochlorite solution for 15 min followed by washing with sterile water 5-6 times, and blow-drying on sterile filter paper to obtain aseptic seeds. Then the aseptic seeds were inoculated, by sterile tweezers, into a germination culture medium for dark culture, and the germination culture medium was an MS culture medium containing 3 wt. % of sucrose, 1.0 mg/L of 6-BA, and 0.8 wt. % of agar, and had a pH of 5.8. The dark culture is performed at a day temperature of 24° C., a night temperature of 18° C. and a humidity of 80%. After 60 h of the dark culture, germinated seeds were collected. Testa, root tip, two cotyledons and middle growing point of the two cotyledons from each of the germinated seeds were removed by a scalpel. And embryonic tips of the germinated seeds with a length of about 3-5 mm were retained as explants. The explants were subjected into a pre-culture medium for low-temperature pre-culture to obtain primarily-cultured explants. The pre-culture medium was an MS culture medium containing 3 wt. % of sucrose, 2.0 mg/L of 6-BA, 0.4 mg/L of 2,4-D and 0.8 wt. % of agar, and had a pH of 5.8. Culture conditions of the pre-culture were listed as follows: culture time: 36 h; day temperature: 18° C.; night temperature: 12° C.; day light-exposure length: 16 hours; night light-exposure length: 8 hours; light intensity: 3000 Lx; and humidity: 80%. And finally, the primarily-cultured explants were collected and analyzed as follows.

(1) Influence of Bud Induction Culture Medium Component on Adventitious Bud Induction of Embryonic Tip Explants The explants were divided into multiple groups and were inoculated into bud induction culture mediums with different concentrations of 6-BA, NAA and isopentenyl adenine for bud induction, and the bud induction culture mediums were MS culture medium containing 3 wt. % of sucrose, 0.5-1.0 mg/L of 6-BA, 0.1-0.3 NAA, 0-3 mg/L of isopentenyl adenine and 0.8 wt. % agar with a pH of 5.8. Culture conditions of the bud induction were listed as follows: day temperature: 24° C.; night temperature: 18° C.; day light-exposure length: 16 h; night light-exposure length: 8 h; light intensity: 3000 Lx; and humidity: 80%. For individual groups, at least 30 explants were selected, and each treatment was performed in triplicate. Adventitious buds germinated after 20 d culture, and induction efficiency of adventitious buds were measured.

TABLE 5

Influence of Different Hormone Combination on Adventitious Bud Induction of Embryonic Tip Explants

| 6-BA (mg/L) | NAA (mg/L) | Isopentenyl adenine (mg/L) | Induction efficiency of adventitious buds (%) | Average number of adventitious buds per explants |
| --- | --- | --- | --- | --- |
| 0.8 | 0.2 | 0 | 70.40 ± 1.18 a | 6.03 ± 0.15 a |
| 0.5 | 0.1 | 1 | 38.37 ± 0.55 e | 2.87 ± 0.24 d |
| 0.5 | 0.2 | 3 | 41.17 ± 0.69 de | 3.13 ± 0.23 d |
| 0.5 | 0.3 | 2 | 37.20 ± 2.51 e | 3.10 ± 0.23 d |
| 0.8 | 0.1 | 3 | 48.97 ± 2.96 c | 4.47 ± 0.26 bc |
| 0.8 | 0.2 | 2 | 73.67 ± 1.14 a | 5.97 ± 0.20 a |
| 0.8 | 0.3 | 1 | 57.90 ± 2.73 b | 5.17 ± 0.12 ab |
| 1 | 0.1 | 2 | 53.33 ± 3.47 bc | 4.10 ± 0.42 c |
| 1 | 0.2 | 1 | 47.10 ± 2.25 cd | 2.97 ± 0.52 d |
| 1 | 0.3 | 3 | 38.10 ± 3.93 e | 3.17 ± 0.19 d |

The letters "a", "b", "c", "d" and "e" indicate significant difference at $P<0.05$.

Referring to Table 5, different combinations of 6-BA, NAA and isopentenyl adenine have different induction efficiency of adventitious buds. The induction efficiency of adventitious buds is the highest with 0.8 mg/L of 6-BA and 0.2 mg/L of NAA, and there is no significant difference in the induction efficiency of adventitious buds when isopentenyl adenine is 2.0 mg/L or 0 mg/L, which indicates that addition of isopentenyl adenine in the bud induction culture medium has no significant influence on the induction efficiency of adventitious buds of embryonic tip of *Brassica campestris* L. ssp. *chinensis*. And subsequent experiments were conducted in the bud induction culture medium, that is, an MS culture medium containing 3 wt. % of sucrose, 0.8 mg/L of 6-BA, 0.2 mg/L of NAA and 0.8 wt. % agar with a pH of 5.8 for adventitious bud induction.

(2) Influence of Liquid Short-Time Culture on Adventitious Bud Induction of Embryonic Tip Explants Multiple groups of the primarily-cultured explants were transferred into a liquid bud induction culture medium, and the liquid bud induction culture medium was an MS culture medium containing 3 wt. % of sucrose, 0.8 mg/L of 6-BA, 0.2 mg/L of NAA and 2 mg/L of isopentenyl adenine, and has a pH of 5.8. The primarily-cultured explants were subjected to shaking culture at room temperature for 0-20 min with a rotating speed of 180 rpm. Then the primarily-cultured explants were transferred into the bud induction culture medium for bud induction, and the bud induction culture medium was an MS culture medium containing 3 wt. % of sucrose, 0.8 mg/L of 6-BA, 0.2 mg/L of NAA and 0.8% agar, and has a pH of 5.8. Culture conditions of the bud induction were listed as follows: day temperature: 24° C.; night temperature: 18° C.; day light-exposure length: 16 hours; night light-exposure length: 8 hours; light intensity: 3000 Lx; and humidity: 80%. For individual groups, at least 30 explants were selected, and each treatment was performed in triplicate. Adventitious buds germinated after 20 d culture, and induction efficiency of adventitious buds were measured.

TABLE 6

Influence of Culture Duration of Liquid Bud Induction Culture Medium on Adventitious Bud Induction of Embryonic Tip

| Liquid culture duration (min) | Induction efficiency of adventitious buds (%) | Average number of adventitious buds per explants |
|---|---|---|
| 0 | 48.53 ± 0.84 e | 5.23 ± 0.15 d |
| 5 | 66.03 ± 3.27 c | 6.20 ± 0.25 c |
| 10 | 90.47 ± 1.68 a | 8.77 ± 0.12 a |
| 15 | 76.53 ± 1.16 b | 7.23 ± 0.19 b |
| 20 | 59.80 ± 0.40 d | 6.10 ± 0.31 c |

The letters "a", "b", "c", "d" and "e" indicate significant difference at $P<0.05$.

Referring to Table 6, the induction efficiency of adventitious buds is highest (90.47%) when is cultured in the liquid bud induction culture medium for 10 min, and in this condition, the average number of adventitious buds per explants is 8.77. The induction efficiency of adventitious buds is significantly higher than that without inducting in the liquid bud induction culture medium (48.53%, Table 6) and that in solid bud induction culture medium with isopentenyl adenine (73.67%, Table 5).

In subsequent experiments, the primarily-cultured explants were selected, subjected to shaking culture at room temperature in the liquid bud induction culture medium, that is the MS culture medium containing 3% of sucrose, 0.8 mg/L of 6-BA, 0.2 mg/L of NAA, 2 mg/L of isopentenyl adenine with the pH of 5.8, and transferred into the bud induction culture medium, that is, the MS culture medium containing 3 wt. % of sucrose, 0.8 mg/L of 6-BA, 0.2 mg/L of NAA and 0.8 wt. % of agar with the pH of 5.8, for adventitious bud induction.

Embodiment 4 Influence of Rooting Culture Medium Component on Regenerated Plant Rooting In this embodiment, plump and consistent seeds of *Brassica campestris* L. ssp. *chinensis* var. *communis* were selected, washed with sterile water twice and disinfected by blowing with a pipette with 70% of alcohol for 30 s. Then the seeds were shaken and soaked with a 2 wt. % of sodium hypochlorite solution for 15 min followed by washing with sterile water 5-6 times, and blow-drying on sterile filter paper to obtain aseptic seeds. Then the aseptic seeds were inoculated, by sterile tweezers, into a germination culture medium for dark culture, and the germination was an MS culture medium containing 3 wt. % of sucrose, 1.0 mg/L of 6-BA and 0.8 wt. % of agar, and had a pH of 5.8. And the dark culture was performed at a day temperature of 24° C., a night temperature of 18° C. and a humidity of 80%. After 60 h of the dark culture, germinated seeds were collected. Testa, root tip, two cotyledons and middle growing point of the two cotyledons from each of the germinated seeds were removed by a scalpel. And embryonic tips of the germinated seeds with a length of about 3-5 mm were retained as explants. The explants were subjected to low-temperature pre-culture in a pre-culture medium for 36 h to obtain primarily-cultured explants, and the pre-culture medium was an MS culture medium containing 3 wt. % of sucrose, 2.0 mg/L of 6-BA, 0.4 mg/L of 2,4-D and 0.8 wt. % of agar, and had a pH of 5.8. Culture conditions of the pre-culture were listed as follows: day temperature: 18° C.; night temperature: 12° C.; day light-exposure length: 16 hours; night light-exposure length: 8 hours; light intensity: 3000 Lx; and humidity: 80%. The primarily-cultured explants were collected and transferred into a first bud induction culture medium for shaking culture at room temperature for 10 min to obtain secondarily-cultured explants, and the first bud induction culture medium was an MS culture medium containing 3 wt. % of sucrose, 0.8 mg/L of 6-BA, 0.2 mg/L of NAA and 2 mg/L of isopentenyl adenine, and had a pH of 5.8. The secondarily-cultured explants were transferred into a second bud induction culture medium for bud induction, and the second bud induction culture medium was an MS culture medium containing 0.8 mg/L of 6-BA, 0.2 mg/L of NAA, 0.8 wt. % of agar and 3% of sucrose, and had a pH of 5.8. Culture conditions of the bud induction were listed as follows: culture time: about 20 days; day temperature: 24° C.; night temperature: 18° C.; day light-exposure length: 16 hours; night light-exposure length: 8 hours; light intensity: 3000 Lx; and humidity: 80%.

Regenerated plants with 5-6 leaves from steps above were collected, divided in multiple groups and inoculated into rooting culture mediums with a certain concentration of IBA for rooting culture. The rooting culture mediums were MS culture mediums containing 3 wt. % of sucrose, 0.5-1.5 mg/L of IBA, 0.8 wt. % of agar, and had a pH of 5.8, and an optimum formulation of the rooting culture mediums was determined. And culture conditions of the rooting culture were listed as follows: culture time: day temperature: 24° C.; night temperature: 18° C.; day light-exposure length: 16 hours; night light-exposure length: 8 hours; light intensity: 3000 Lx; and humidity: 80%.

TABLE 7

Influence of Different IBA Concentration on Adventitious Bud Rooting

| IBA concentration (mg/L) | Rooting efficiency |
|---|---|
| 0.5 | 76.10 ± 2.52 b |
| 1.0 | 94.73 ± 1.94 a |
| 1.5 | 81.83 ± 0.32 b |

The letters "a" and "b" indicate significant difference at $P<0.05$.

Referring to Table 7, the rooting efficiency is the highest of 94.73% when the IBA concentration is 1.0 mg/L. MS culture mediums with 1.0 mg/L of IBA were selected as the rooting culture medium for subsequent experiments.

In conclusion, the aseptic seeds were subjected into the germination culture medium, the MS culture medium containing 3 wt. % of sucrose, 1.0 mg/L of 6-BA, 0.8 wt. % of agar with the pH of 5.8, for dark culture, and the dark culture was performed at the day temperature of 24° C., the night temperature of 18° C., and the humidity of 80%. Embryonic tips of the germinated seeds form 60 h culture were collected and subjected into the pre-culture medium, the MS culture medium containing 3 wt. % of sucrose, 2.0 mg/L of 6-BA, 0.4 mg/L of 2,4-D and 0.8% agar with the pH of 5.8, for low-temperature pre-culture for 36 h to obtain primarily-cultured explants, and culture conditions of the low-temperature pre-culture were listed as follows: day temperature: 18° C.; night temperature: 12° C.; day light-exposure length: 16 hours; night light-exposure length: 8 hours; light intensity: 3000 Lx; and humidity: 80%. The primarily-cultured explants were collected and transferred into the first bud induction culture medium, the MS medium culture containing 3 wt. % of sucrose, 0.8 mg/L of 6-BA, 0.2 mg/L of NAA and 2 mg/L of isopentenyl adenine with pH of 5.8, for shaking culture at room temperature for 10 min to obtain secondarily-cultured explants, and immediately transferred into the second bud induction culture medium, the MS culture medium containing 0.8 mg/L of 6-BA, 0.2 mg/L of NAA, 0.8 wt. % of agar, 3 wt. % of sucrose with the pH of 5.8, for bud induction. Regeneration efficiency of embryonic tips of *Brassica campestris* L. ssp. *chinensis* reaches 90.47% and the average number of adventitious buds per explants is 8.77. Then the regenerated seedlings were transferred into the rooting culture medium, the MS culture medium containing 3 wt. % of sucrose, 1.0 mg/L of IBA, 0.8 wt. % of agar with the pH of 5.8, for rooting culture, and rooting efficiency can reach 94.72%. Finally, the regenerated seedlings were collected and subjected to hardening and transplantation, and survival rate can reach above 90%.

Embodiment 5 Comparison of Embryonic Tip Tissue Culture Efficiency of *Brassica campestris* L. Ssp. *Chinensis* with Different Genotypes Regeneration system of embryonic tips of *Brassica campestris* L. ssp. *Chinensis* obtained in Embodiment 4 were used. 4 representative varieties of *Brassica campestris* L. ssp. *chinensis* were selected for embryonic tip regeneration, and the regeneration efficiency and the number of adventitious buds were compared. Results are shown in Table 8.

TABLE 8

Comparison of Regeneration Efficiency of Different Varieties of *Brassica campestris* L. ssp. *chinensis*

| Varieties of *Brassica campestris* L. ssp. *chinensis* | Regeneration Efficiency (%) | Average number of adventitious buds per explants |
|---|---|---|
| *Brassica campestris* L. ssp. *chinensis* var. *communis* | 90.47 ± 1.68 | 8.77 ± 0.12 |
| Black heart cabbage | 89.80 ± 2.62 | 7.47 ± 0.48 |
| Xiaobaye Chinese cabbage | 71.17 ± 2.39 | 7.57 ± 0.69 |
| Zhongbaye Chinese cabbage | 88.37 ± 2.90 | 6.30 ± 0.52 |

Referring to Table 8, for the regeneration culture with explants of different genotypes, high regeneration efficiency of adventitious buds and the average number of adventitious buds per explants were obtained, indicating that the regeneration system of *Brassica campestris* L. ssp. *chinensis* can be applied to other genotypes of materials.

In order to compare advantaged and disadvantages of tissue culture, such as embryonic tips and hypocotyls, experiments were carried out as follows.

Comparative Example 1 Method for Quickly Obtaining Regeneration Seedlings of *Brassica campestris* L. ssp. *Chinensis* from Tissue Culture of Hypocotyl (S1) Preparation of Explant Materials Plump and consistent seeds of *Brassica campestris* L. ssp. *chinensis* var. *communis* were selected, washed with sterile water twice and disinfected by blowing with a pipette with 70% alcohol for 30 s. Then the seeds were shaken and soaked with a 2 wt. % of sodium hypochlorite solution for 15 min followed by washing with sterile water 5-6 times, and blow-drying on sterile filter paper to obtain aseptic seeds. Then the aseptic seeds were inoculated, by sterile tweezers, into MS culture mediums containing 0-2 mg/L of 6-BA, 3 wt. % of sucrose and 0.8 wt. % of agar with a pH of 5.8 for dark culture. The dark culture was performed at a day temperature of 24° C. and a night temperature of 18° C. Hypocotyls of 4 d seedling age were collected and subjected into an MS culture medium containing 5 mg/L of 6-BA for pre-culture for 2 d, and then transferred into an MS culture medium containing 3 mg/L of 6-BA, 0.1 mg/L of NAA and 1.0 mg/L of isopentenyl adenine for bud induction culture. Bud induction efficiency and average number of adventitious buds per explants were observed, and influence of seed germination culture medium on hypocotyl of adventitious bud induction was analyzed. For individual groups, at least 30 explants are selected, and each treatment is performed in triplicate. And the MS culture medium was added with 3 wt. % of sucrose and 0.8 wt. % of agar at a pH of 5.8, and culture conditions of the adventitious bud induction were listed as follows: day temperature: 24° C.; night temperature: 18° C.; day light-exposure length: 16 hours; night light-exposure length: 8 hours; light intensity: 3000 Lx; and humidity: 80%.

TABLE 9

Influence of Seed Germination Culture Medium on Hypocotyl of Adventitious Bud

| 6-BA concentration (mg/L) | Induction efficiency of adventitious buds (%) | Average number of adventitious buds per explants |
|---|---|---|
| 0 | 9.15 ± 2.95 b | 1.92 ± 0.39 a |
| 1 | 22.67 ± 1.95 a | 1.23 ± 0.03 a |
| 2 | 12.23 ± 0.13 b | 1.00 ± 0.00 a |

The letters "a" and "b" indicate significant difference at $P<0.05$.

Referring to Table 9, when the seed germination culture medium was an MS culture medium containing 1.0 mg/L of 6-BA, the induction efficiency of adventitious buds reaches 22.67%. But there is no significant difference in the average number of adventitious buds per explants with different 6-BA concentrations. The MS culture medium containing 1.0 mg/L 6-BA were selected for subsequent experiments.

(2) Pre-Culture for Hypocotyl Explants

The seedlings of 4 d seedling age were obtained in step (1), and hypocotyls with about 3-5 mm were cut. The hypocotyls were inoculated into an MS culture medium containing 2-6 mg/L of 6-BA and 0.2-0.6 mg/L of 2,4-D to culture for 24-48 h, then were transferred into an MS culture medium containing 3 mg/L of 6-BA, 0.1 mg/L of NAA and 1.0 mg/L of isopentenyl adenine to culture. Bud induction efficiency and the average number of adventitious buds per explants were observed, and influence of pre-culture on hypocotyl explants was studied. For individual groups, at least 30 explants were selected, and each treatment was performed in triplicate. And the MS culture medium was added with 3 wt. % of sucrose and 0.8 wt. % of agar at a pH of 5.8. And the culture was performed at a day temperature of 18° C., a night temperature of 12° C., a day light-exposure length of 16 h, a night light-exposure length of 8 h, a light intensity of 3000 Lx, and a humidity 80%.

TABLE 10

Influence of Pre-culture on Hypocotyl of Adventitious Bud

| 6-BA concentration (mg/L) | 2,4-D concentration (mg/L) | Time (h) | Induction efficiency of adventitious buds (%) | Average number of adventitious buds per explants |
|---|---|---|---|---|
| 2 | 0.2 | 24 | 5.43 ± 1.07 e | 1.30 ± 0.06 c |
| 2 | 0.4 | 48 | 8.80 ± 1.20 e | 2.13 ± 0.20 b |
| 2 | 0.6 | 36 | 17.87 ± 2.73 d | 2.33 ± 0.19 b |
| 4 | 0.2 | 48 | 22.77 ± 1.68 c | 2.37 ± 0.12 b |
| 4 | 0.4 | 36 | 39.13 ± 0.90 a | 3.00 ± 0.10 a |
| 4 | 0.6 | 24 | 32.40 ± 1.99 b | 2.10 ± 0.12 b |
| 6 | 0.2 | 36 | 27 . . . 07 ± 0.67 c | 2.37 ± 0.13 b |
| 6 | 0.4 | 24 | 24.27 ± 1.60 c | 2.17 ± 0.07 b |
| 6 | 0.6 | 48 | 17.47 ± 0.75 d | 1.57 ± 0.12 c |

The letters "a", "b", "c", "d" and "e" indicate significant difference at $P<0.05$.

Referring to Table 10, when the pre-culture was performed with 4 mg/L of 6-BA and 0.4 mg/L of 2,4-D for 36 h, the induction efficiency of adventitious buds is the highest which is 39.13%, and the average number of adventitious buds per explants is 3.00. Subsequent experiments were conducted with 4 mg/L of 6-BA and 0.4 mg/L of 2,4-D.

(3) The hypocotyls from step (2) were transferred into MS culture mediums containing 0-1.0 mg/L of 6-BA, 0-1.0 mg/L of NAA and 0-3 mg/L of isopentenyl adenine. Each treatment was performed in triplicate each involving at least 30 explants to study the adventitious bud induction. Adventitious buds formed after 35 d culture, and the induction rate of explants was measured.

TABLE 11

Influence of Different Hormone Combinations on the induction of Adventitious Bud from Hypocotyl

| 6-BA concentration (mg/L) | 2,4-D concentration (mg/L) | Isopentenyl adenine (mg/L) | Induction efficiency of adventitious buds (%) | Average number of adventitious buds per explant |
|---|---|---|---|---|
| 1 | 0.5 | 0 | 13.97 ± 0.73 e | 1.20 ± 0.10 c |
| 0 | 0 | 1 | 13.17 ± 1.04 e | 1.80 ± 0.12 c |
| 0 | 0.5 | 3 | 24.43 ± 1.03 c | 1.63 ± 0.12 c |
| 0 | 1 | 2 | 18.20 ± 1.59 d | 1.63 ± 0.24 c |
| 0.5 | 0 | 3 | 23.93 ± 0.71 c | 1.13 ± 0.09 c |
| 0.5 | 0.5 | 2 | 34.77 ± 1.83 b | 1.73 ± 0.27 c |
| 0.5 | 1 | 1 | 24.83 ± 2.47 c | 2.50 ± 0.12 b |
| 1 | 0 | 2 | 36.00 ± 1.80 b | 2.73 ± 0.19 ab |
| 1 | 0.5 | 1 | 45.73 ± 1.22 a | 3.23 ± 0.20 a |
| 1 | 1 | 3 | 38.97 ± 0.54 b | 2.47 ± 0.43 b |

The letters "a", "b", "c", "d" and "e" indicate significant difference at $P<0.05$.

Referring to Table 11, different hormone combinations have significant influence on adventitious buds from hypocotyl. When the isopentenyl adenine is 0 mg/L, the induction efficiency of adventitious buds is significantly decreased, indicating that isopentenyl adenine can significantly improves hypocotyl regeneration efficiency of *Brassica campestris* L. ssp. *chinensis*. The induction efficiency of adventitious buds, with 1.0 mg/L of 6-BA, 0.5 mg/L of NAA and 1.0 mg/L of isopentenyl adenine, is the highest which is 45.73%, and the average number of adventitious buds per explants is 3.23. Subsequent experiments were conducted in a bud induction culture medium containing 1.0 mg/L of 6-BA, 0.5 mg/L of 2,4-D and 1.0 mg/L of isopentenyl adenine.

(4) Rooting Culture for Adventitious Buds

A method for rooting, seedling hardening and transplantation of hypocotyls are the same as that of embryonic tips.

Combined with optimization conditions above, the aseptic seeds were subjected into an MS culture medium containing 1.0 mg/L of 6-BA to culture. The aseptic seedlings of 4 d seedling age were cut to obtain about 3-5 mm of hypocotyls. The hypocotyls were subjected into an MS culture medium with 4 mg/L of 6-BA and 0.4 mg/L of 2,4-D for low-temperature pre-culture for 36 h and then transferred into an MS culture medium containing 1.0 mg/L of 6-BA, 0.5 mg/L of NAA and 1.0 mg/L of isopentenyl adenine. The regeneration efficiency of hypocotyls of *Brassica campestris* L. ssp. *chinensis* can reach 45.73% and the average number of adventitious buds per explants is 3.23.

In order to compare advantages and disadvantages between embryonic tip tissue culture and cotyledon-cotyledon petiole tissue culture, experiments were conducted as follows.

Comparative Example 2 Method for Quickly Obtaining Regeneration Seedlings of *Brassica campestris* L. Ssp. *Chinensis* from Tissue Culture of Cotyledon-Cotyledon Petiole (1) Preparation of Explant Materials Plump and consistent seeds of *Brassica campestris* L. ssp. *chinensis* var. *communis* were selected, washed with sterile water twice and disinfected by blowing with a pipette with 70% of alcohol for 30 s. Then the seeds were shaken and soaked with a 2 wt. % of sodium hypochlorite solution for 15 min followed by washing with sterile water 5-6 times, and blow-drying on sterile filter paper to obtain aseptic seeds. Then the aseptic seeds are inoculated, by sterile tweezers, into MS culture mediums containing 0-2 mg/L of 6-BA, 3 wt. % of sucrose and 0.8 wt. % of agar with a pH of 5.8, for dark culture. The dark culture was performed at a day temperature of 24° C., a night temperature of 18° C. Cotyledon-cotyledon petioles of 4 d seedling age were collected and subjected into an MS culture medium containing 3.0 mg/L of 6-BA for pre-culture for 2 d, and then transferred into an MS culture medium containing 2.0 mg/L of 6-BA, 0.1 mg/L of NAA, 1.0 mg/L of isopentenyl adenine for bud culture. Bud induction efficiency and average number of adventitious buds per explants were observed, and influence of seed germination culture medium on cotyledon-s of adventitious bud induction was analyzed. For individual groups, at least 30 explants were selected, and each treatment was performed in triplicate. And the MS culture medium was added with 3 wt. % of sucrose and 0.8 wt. % of agar at a pH of 5.8, and culture conditions of the bud culture were listed as follows: day temperature: 24° C.; night temperature: 18° C.; day light-exposure length: 16 hours; night light-exposure length: 8 hours; light intensity: 3000 Lx; and humidity: 80%.

TABLE 12

Influence of Seed Germination Culture Medium on Cotyledon- s of Adventitious Bud

| 6-BA concentration (mg/L) | Induction efficiency of adventitious buds (%) | Average number of adventitious buds per explants |
|---|---|---|
| 0 | 29.80 ± 0.93 b | 1.70 ± 0.15 b |
| 1 | 44.90 ± 1.84 a | 2.30 ± 0.15 a |
| 2 | 33.10 ± 2.36 b | 1.57 ± 0.09 b |

The letters "a" and "b" indicate significant difference at $P<0.05$.

Referring to Table 12, when the seed germination culture medium is an MS culture medium added with 1 mg/L of 6-BA, the induction efficiency of adventitious buds can reach 44.90%, and the average number of adventitious buds per explants is 2.30. Seed germination culture medium containing 1.0 mg/L of 6-BA were selected for subsequent experiments.

(2) Pre-Culture of Cotyledon-Cotyledon Petiole Explants

The aseptic seedlings of 4 d seedling age were obtained in step (S1), and cotyledon explants with about 1-2 mm of cotyledon petiole were cut by a scalpel. Cotyledon-s were inoculated into MS culture mediums containing 2-6 mg/L of 6-BA, 0.2-0.6 mg/L of 2,4-D culture medium to culture for 24-48 h, then were transferred into an MS culture medium containing 2 mg/L of 6-BA, 0.1 mg/L of NAA and 1.0 mg/L of isopentenyl adenine to culture. Bud induction efficiency and average number of adventitious buds per explants were observed, and influence of pre-culture on the cotyledon-s was analyzed. For individual groups, at least 30 explants were selected, and each treatment was performed in triplicate.

TABLE 13

Influence of Pre-culture on Cotyledon- Explants

| 6-BA concentration (mg/L) | 2,4-D concentration (mg/L) | Time (h) | Induction efficiency of adventitious buds (%) | Average number of adventitious buds per explants |
|---|---|---|---|---|
| 2 | 0.2 | 24 | 29.47 ± 0.95 e | 1.80 ± 0.25 d |
| 2 | 0.4 | 48 | 28.07 ± 3.32 e | 2.03 ± 0.32 d |
| 2 | 0.6 | 36 | 42.30 ± 0.78 bc | 2.73 ± 0.20 c |
| 4 | 0.2 | 48 | 43.67 ± 4.17 bc | 2.17 ± 0.12 d |
| 4 | 0.4 | 36 | 53.73 ± 2.36 a | 4.27 ± 0.09 a |
| 4 | 0.6 | 24 | 47.97 ± 1.32 ab | 3.13 ± 0.13 bc |
| 6 | 0.2 | 36 | 39.17 ± 0.90 cd | 3.53 ± 0.09 b |
| 6 | 0.4 | 24 | 38.33 ± 1.47 cd | 3.20 ± 0.17 bc |
| 6 | 0.6 | 48 | 33.90 ± 1.70 de | 2.90 ± 0.10 c |

The letters "a", "b", "c", "d" and "e" indicate significant difference at $P<0.05$.

Table 13 shows influence of pre-culture on induction efficiency of adventitious buds of cotyledon-. When the pre-culture is performed with 4 mg/L of 6-BA and 0.4 mg/L of NAA for 36 h, the induction efficiency of adventitious buds is the highest of 53.73%, and the average number of adventitious buds per explants is 4.27. Subsequent experiments were conducted with 4 mg/L of 6-BA and 0.4 mg/L of 2,4-D for 36 h.

(3) Bud Induction Culture of Cotyledon-Cotyledon Petiole Explants

The cotyledon—from step (S2) were transferred into MS culture mediums containing 0-1.0 mg/L of 6-BA, 0-1.0 mg/L of NAA and 0-3 mg/L of isopentenyl adenine. For individual groups, at least 30 explants were selected, and each treatment was performed in triplicate to study adventitious bud induction. Adventitious buds germinated after 35 d culture. And induction rate of explants was measured.

In order to improve regeneration efficiency of cotyledon—and obtain more regeneration seedlings, the cotyledon-cotyledon petioles with adventitious buds from above were subjected to subculture, and a subculture medium was an MS culture medium containing 0.5 mg/L of Gibberellin A3 (GA3), where the subculture medium was added with 3 wt. % of sucrose and 0.8 wt. % of agar at a pH of 5.8, and culture conditions of the subculture were listed as follows: day temperature: 24° C.; night temperature: 18° C.; day light-exposure length: 16 hours; night light-exposure length: 8 hours; light intensity: 3000 Lx; and humidity: 80%.

TABLE 14

Influence of Different Hormone Combinations on Adventitious Bud from Cotyledon-cotyledon petiole

| 6-BA concentration (mg/L) | 2,4-D concentration (mg/L) | Isopentenyl adenine (mg/L) | Induction efficiency of adventitious buds (%) | Average number of adventitious buds per explants |
|---|---|---|---|---|
| 1   | 0.5 | 0 | 8.60 ± 1.11 f  | 2.27 ± 0.09 c  |
| 0   | 0   | 1 | 10.43 ± 0.64 f | 2.73 ± 0.44 c  |
| 0   | 0.5 | 3 | 25.27 ± 1.02 e | 2.57 ± 0.29 c  |
| 0   | 1   | 2 | 22.27 ± 1.46 e | 2.37 ± 0.17 c  |
| 0.5 | 0   | 3 | 52.63 ± 1.89 b | 2.40 ± 0.40 c  |
| 0.5 | 0.5 | 2 | 31.93 ± 3.22 d | 3.77 ± 0.15 b  |
| 0.5 | 1   | 1 | 45.73 ± 1.22 c | 4.07 ± 0.47 b  |
| 1   | 0   | 2 | 57.23 ± 1.23 b | 4.23 ± 0.22 ab |
| 1   | 0.5 | 1 | 66.47 ± 3.43 a | 5.07 ± 0.20 a  |
| 1   | 1   | 3 | 57.13 ± 2.08 b | 3.70 ± 0.32 b  |

The letters "a", "b", "c", "d", "e" and "f" indicate significant difference at P<0.05.

Referring to Table 14, different hormone combinations have significant influence on adventitious buds from cotyledon-s. When the isopentenyl adenine is 0 mg/L, the induction efficiency of adventitious buds is significantly decreased, indicating that isopentenyl adenine can significantly improves regeneration efficiency of cotyledon— of *Brassica campestris* L. ssp. *chinensis*. The induction efficiency of adventitious buds, with 1.0 mg/L of 6-BA, 0.5 mg/L of NAA and 1.0 mg/L of isopentenyl adenine, is the highest which is 66.47%, and the average number of adventitious buds per explants is 5.07. Subsequent experiments were conducted in a bud induction culture medium containing 1.0 mg/L of 6-BA and 0.5 mg/L of 2,4-D and 1.0 mg/L of isopentenyl adenine.

(4) Rooting Culture for Cotyledon-Cotyledon Petiole Explants

A method for rooting, seedling hardening and transplantation of cotyledon-s are the same as that of embryonic tips.

Combined with optimization conditions above, the aseptic seeds were subjected into an MS culture medium containing 1.0 mg/L 6-BA to culture. The aseptic seedlings of 4 d seedling age were cut to obtain cotyledon-s. The cotyledon-s were subjected into an MS culture medium containing 4 mg/L of 6-BA and 0.4 mg/L 2,4-D for low-temperature pre-culture for 36 h and then transferred into an MS induction culture medium containing 1.0 mg/L of 6-BA, 0.5 mg/L of NAA and 1.0 mg/L of isopentenyl adenine. The regeneration efficiency of cotyledon-s of *Brassica campestris* L. ssp. *chinensis* can reach 66.47% and the average number of adventitious buds per explants is 5.07.

According to Embodiments 1-4 and Comparative examples 1-2, the regeneration efficiency, the average number of adventitious buds per explants and the adventitious bud induction duration are compared, and results are shown in Table 15.

TABLE 15

Regeneration Efficiency Comparison of Different Explants of *Brassica campestris* L. ssp. *chinensis*

| Explant | Regeneration efficiency (%) | Average number of adventitious buds per explants | Adventitious bud induction time (d) |
|---|---|---|---|
| Embryonic tip | 90.47 ± 1.68 a | 8.77 ± 0.12 a | 20 |
| Hypocotyl | 45.73 ± 1.22 c | 3.23 ± 0.20 c | 35 |
| Cotyledon-cotyledon petiole | 66.47 ± 3.43 b | 5.07 ± 0.20 b | 30 |

The letters "a", "b" and "c" indicate significant difference at P<0.05.

Referring to Table 14, among three explants of *Brassica campestris* L. ssp. *chinensis* above, embryonic tips has the highest regeneration efficiency, reaching 90.47% and most average number of adventitious buds per explants, followed by the regeneration efficiency of cotyledon-, reaching 66.47%, and the regeneration efficiency of hypocotyl is the worst which is 45.73%. In addition, the regeneration time of embryonic tip is the shortest, which can be inducted regeneration buds in 20 d, while hypocotyl and cotyledon-cotyledon petiole need longer time to induce differentiation of adventitious bud, indicating that embryonic tip is the best type of explant of regeneration system of *Brassica campestris* L. ssp. *chinensis*.

Described above are only preferred embodiments of the disclosure, and are not intended to limit the scope of this application. Any modifications, equivalent replacements and improvements made by those skilled in the art within the spirit and principle of this application shall fall within the scope of this application defined by the appended claims.

What is claimed is:

1. A method for obtaining regenerated seedlings of *Brassica campestris* L. ssp. *chinensis* from an embryonic tip tissue, comprising:
    (S1) obtaining an aseptic seed of *Brassica campestris* L. ssp. *chinensis*;
    (S2) inoculating the aseptic seed obtained in step (S1) into a germination culture medium for dark culture for 60 hours, wherein the germination culture medium is a Murashige and Skoog (MS) culture medium containing 3 wt. % of sucrose, 1.0 mg/L of 6-benzylaminopurine (6-BA) and 0.8 wt. % agar, and has a pH of 5.8, and the dark culture is performed at a day temperature of 24° C., a night temperature of 18° C. and a humidity of 80%;

(S3) collecting a germinated seed, removing testa, root tip, two cotyledons and middle growing point from the germinated seed, retaining an embryonic tip with a length of 3-5 mm as an explant;

(S4) subjecting the explant to pre-culture in a pre-culture medium for 36 hours to obtain a primarily-cultured explant, wherein the pre-culture is performed at a day temperature of 18° C., a night temperature of 12° C., and a humidity of 80%, and wherein the pre-culture medium is an MS culture medium containing 3 wt. % of sucrose, 2.0 mg/L of 6-BA, 0.4 mg/L of 2,4-dichlorophenoxyacetic acid (2,4-D) and 0.8 wt. % of agar, and has a pH of 5.8;

(S5) subjecting the primarily-cultured explant to shaking culture in a first bud induction culture medium to obtain a secondarily-cultured explant, wherein the shaking culture is performed at room temperature under a rotating speed of 180 rpm for 10 min, and wherein the first bud induction culture medium is an MS culture medium containing 3 wt. % of sucrose, 0.8 mg/L of 6-BA, 0.2 mg/L of naphthaleneacetic acid (NAA) and 2 mg/L of isopentenyladenine, and has a pH of 5.8;

(S6) transferring the secondarily-cultured explant to a second bud induction culture medium for bud induction, wherein the second bud induction culture medium is an MS culture medium containing 0.8 mg/L of 6-BA, 0.2 mg/L of NAA, 0.8 wt. % of agar and 3 wt. % of sucrose, and has a pH of 5.8, and wherein culture conditions of the bud induction are listed as follows: culture time: 20 days; day temperature: 24° C.; night temperature: 18° C.; day light-exposure length: 16 hours; night light-exposure length: 8 hours; and humidity: 80%;

(S7) collecting a regenerated plant with 5-6 leaves, and transferring the regenerated plant to a rooting culture medium for rooting culture, wherein the rooting culture medium is an MS culture medium containing 3 wt. % of sucrose, 1.0 mg/L of indole butyric acid (IBA) and 0.8 wt. % of agar, and has a pH of 5.8, and wherein culture conditions of the rooting culture are listed as follows: culture time: 2 weeks; day temperature: 24° C.; night temperature: 18° C.; day light-exposure length: 16 hours; night light-exposure length: 8 hours; and humidity: 80%; and (S8) collecting a rooted plant, and subjecting the rooted plant to hardening followed by transplantation into a field.

* * * * *